United States Patent
Kim et al.

(10) Patent No.: US 10,588,714 B2
(45) Date of Patent: Mar. 17, 2020

(54) ORTHODONTIC BRACKET

(71) Applicant: DIO Corporation, Busan (KR)

(72) Inventors: Jin Chul Kim, Yangsan-si (KR); Jin Baek Kim, Busan (KR)

(73) Assignee: DIO Corporation, Busan (KR)

( * ) Notice: Subject to any disclaimer, the term of this patent is extended or adjusted under 35 U.S.C. 154(b) by 360 days.

(21) Appl. No.: 15/317,224

(22) PCT Filed: Oct. 5, 2016

(86) PCT No.: PCT/KR2016/011094
§ 371 (c)(1),
(2) Date: Dec. 8, 2016

(87) PCT Pub. No.: WO2018/030576
PCT Pub. Date: Feb. 15, 2018

(65) Prior Publication Data
US 2018/0206939 A1     Jul. 26, 2018

(30) Foreign Application Priority Data

Aug. 9, 2016 (KR) .................. 10-2016-0101282
Aug. 9, 2016 (KR) .................. 10-2016-0101285
Aug. 9, 2016 (KR) .................. 10-2016-0101291

(51) Int. Cl.
*A61C 7/14*     (2006.01)
*A61C 7/00*     (2006.01)
(Continued)

(52) U.S. Cl.
CPC ............ *A61C 7/002* (2013.01); *A61B 5/00* (2013.01); *A61C 7/14* (2013.01); *A61C 7/146* (2013.01);
(Continued)

(58) Field of Classification Search
CPC ................................... A61C 7/146
See application file for complete search history.

(56) References Cited

U.S. PATENT DOCUMENTS 3,521,355 A * 7/1970 Pearlman .......... A61C 7/146
433/3
4,134,208 A * 1/1979 Pearlman .......... A61C 7/146
433/8
(Continued)

FOREIGN PATENT DOCUMENTS

| KR | 10-2013-0106284 A | 9/2013 |
| KR | 10-1349356 B1 | 1/2014 |
| KR | 10-2016-0049698 A | 5/2016 |

OTHER PUBLICATIONS

International Search Report for PCT/KR2016/011094 dated Apr. 24, 2017 from Korean Intellectual Property Office.

*Primary Examiner* — Ralph A Lewis
(74) *Attorney, Agent, or Firm* — Paratus Law Group, PLLC (57) ABSTRACT

A method of manufacturing digital brackets for orthodontics, including: loading an oral scan image obtained corresponding to an internal profile of an oral cavity of a subject and extracting one virtual orthodontic template corresponding to each of tooth images virtually adjusted according to a preset consecutive tooth arrangement structure from a digital library, aligning and disposing each of virtual brackets and a virtual wire of the extracted virtual orthodontic template corresponding to the consecutive tooth arrangement structure of each of the tooth images, and designing each of digital brackets configured to include a jig portion assembled with a top of each of the virtual brackets to surround a top of each of the tooth images and a grip protrusion portion configured to protrude from a top end of the jig portion while being integrated therewith, and three- (Continued)

dimensionally printing each of the digital brackets based on design data.

1 Claim, 5 Drawing Sheets (51) Int. Cl.
    *A61B 5/00*     (2006.01)
    *A61C 9/00*     (2006.01)
    *A61C 13/00*     (2006.01)
    *A61C 13/34*     (2006.01)

(52) U.S. Cl.
    CPC ........ *A61C 9/0046* (2013.01); *A61C 13/0004* (2013.01); *A61C 7/145* (2013.01); *A61C 13/0013* (2013.01); *A61C 13/34* (2013.01)

(56) References Cited

U.S. PATENT DOCUMENTS

| | | | |
|---|---|---|---|
| 9,402,695 B2 * | 8/2016 | Curiel | A61C 7/002 |
| 2007/0031775 A1 * | 2/2007 | Andreiko | A61C 7/146 433/24 |
| 2013/0196279 A1 * | 8/2013 | Curiel | A61C 7/002 433/3 |
| 2015/0238282 A1 | 8/2015 | Kuo et al. | |
| 2016/0228214 A1 * | 8/2016 | Sachdeva | A61C 7/002 |

* cited by examiner

ORTHODONTIC BRACKET

CROSS REFERENCE TO PRIOR APPLICATIONS

This application is a National Stage Patent Application of PCT International Patent Application No. PCT/KR2016/011094 (filed on Oct. 5, 2016) under 35 U.S.C. § 371, which claims priority to Korean Patent Application Nos. 10-2016-0101282 (filed on Aug. 9, 2016), 10-2016-0101285 (filed on Aug. 9, 2016), and 10-2016-0101291 (filed on Aug. 9, 2016), which are all hereby incorporated by reference in their entirety.

TECHNICAL FIELD

The present invention relates to an orthodontic digital bracket using a digital library with improved convenience and precision of manufacturing an orthodontic apparatus, and a method of manufacturing the same.

BACKGROUND ART

Generally, occlusion refers to a state in which teeth at an upper jaw and a lower jaw occlude each other when a mouth is closed. Also, malocclusion means an inaccurate occlusion relationship in which an arrangement of the teeth is not aligned due to a certain cause or an occlusion state of the upper and lower jaws deviates from a normal position and causes functional and aesthetic problems.

Here, although a cause of malocclusion is generally known to be a genetic effect, there are many causes thereof such as shapes or sizes of teeth, environmental influence, bad habits, wrong posture, dental caries, or the like.

Meanwhile, when malocclusion occurs, since tooth arrangement is not aligned, food residue may easily remain between teeth. Also, since it is not easy to tidily manage teeth through properly brushing the teeth, dental plaque increases in an oral cavity and gum diseases such as dental caries, gum infections, or the like easily develop. In addition, due to a tooth that greatly deviates from a normal tooth arrangement or a jaw that is abnormally positioned, teeth may be easily damaged, such as odontoclasis and the like, when an external shock is applied thereto.

Accordingly, orthodontic treatment for treating malocclusion is performed. Here, the orthodontic treatment uses a predisposition of teeth to move when receiving an external force.

In detail, various apparatuses and methods are used in orthodontic treatment depending on causes or a treatment period therefor. For example, the apparatuses may be classified into an apparatus for restraining or enhancing development of upper and lower jawbones and an apparatus for gradually moving teeth to desirable positions. Also, the apparatuses may be classified into a removable apparatus installable in or separable from an oral cavity and a fixable apparatus attached to teeth and detached when treatment is completed.

Meanwhile, one method that is currently most generally used is a fixable treatment method of attaching an apparatus called a bracket to a tooth and moving the tooth using tension of a wire such as an orthodontic steel wire, a rubber band or the like, and it may be generally used in various types of orthodontic treatment.

In detail, brackets are firmly attached to surfaces of teeth that are orthodontic objects and a wire is fixed to connect the brackets with one another. Also, a direction and level of a force applied to the wire is variously adjusted by controlling tension applied to the wire, thereby gradually moving the teeth that are orthodontic objects. Accordingly, the teeth that are orthodontic objects are changed in position and posture by the tension of the wire, and the teeth are gradually moved while orthodontic treatment is performed.

However, since typical orthodontic treatment is executed according to experience of an orthodontist, the orthodontist finely adjusts tooth arrangement by repeating a process of directly pulling or releasing a wire fastened to teeth of a patient without certainty. In this case, since the teeth are adjusted to a preferable tooth arrangement through repeated trial and error, time consumed for orthodontics increases and convenience and pain of the subject are aggravated Also, since much depends on an ability of an orthodontist, typical orthodontic treatment is not objective. Also, since a subject should completely depend on the experience and ability of an orthodontist, it is generally difficult to provide a desirable tooth arrangement state.

In addition, the experience and knowledge of the orthodontist are detailed materials that are data which is difficult to record and differ according to personal abilities and experiences of orthodontists. Due to this, since a desirable tooth arrangement model that is the ultimate object of orthodontics is formed using a subjective point of view or subjective experiences of an orthodontist, orthodontics are not universally and objectively performed.

Meanwhile, a bracket is provided to be substantially uniform with a single size, and one side of a pad portion is formed to be flat and is adhered to a tooth that is an orthodontic object using an adhesive member. Here, since positions of brackets attached to adjacent teeth in the tooth arrangement are irregularly fixed, the tension of the wire is not properly transferred to the teeth that are orthodontic objects.

Due to this, the teeth are not straightened to a desirable arrangement so that satisfaction of the subject is decreased and additional orthodontic operations for straightening the same are repetitively performed, thereby increasing an orthodontic treatment period and orthodontic costs.

DISCLOSURE OF INVENTION

Technical Problem

The present invention provides an orthodontic digital bracket using a digital library with improved convenience and precision of manufacturing an orthodontic apparatus, and a method of manufacturing the same.

Technical Solution

One aspect of the present invention provides a method of manufacturing an orthodontic digital bracket using a digital library, including a first operation of loading an oral scan image obtained corresponding to an internal profile of an oral cavity of a subject and extracting one virtual orthodontic template corresponding to each of tooth images that are virtually adjusted according to a preset consecutive tooth arrangement structure from a digital library, a second operation of aligning and disposing each of virtual brackets and a virtual wire of the extracted virtual orthodontic template corresponding to the consecutive tooth arrangement structure of each of the tooth images that are virtually adjusted, and a third operation of designing each of digital brackets configured to include a jig portion assembled with a top of each of the virtual brackets to surround a top of each of the tooth images and a grip protrusion portion configured to protrude from a top end of the jig portion while being integrated therewith, and three-dimensionally printing each of the digital brackets based on design data.

Another aspect of the present invention provides an orthodontic digital bracket, set from digital external shape information of one virtual orthodontic template extracted from a digital library to correspond to each of tooth images that are virtually adjusted according to a preset consecutive tooth arrangement structure in a loaded oral scan image obtained corresponding to an internal profile of an oral cavity of a subject, including a pad portion including at least one coupling groove portion with one side corresponding to each of teeth of the subject and the other side coupled with a wire configured to provide tension to straighten a position of each of the teeth, a jig portion assembled with and fixed to a top of the pad portion to surround an external surface of a top end of each of the teeth to align a position of the pad portion, and a grip protrusion portion integrated with and protrude from a top end of the pad portion to be gripped.

Advantageous Effects

An orthodontic digital bracket using a digital library and a method of manufacturing the same according to the present invention provide the following effects.

First, since digital external shape information of one virtual orthodontic template corresponding to a preset consecutive tooth arrangement structure of a subject selected among a plurality of virtual orthodontic templates prestored in a digital library to represent personal deviations may be quickly connected to design information of a digital bracket, convenience of manufacturing the digital bracket may be notably increased.

Second, in a case of the virtual orthodontic template, a plurality of virtual brackets are stored as one set, simultaneously arranged in an oral scan image corresponding to the inside of an oral cavity of the subject, and are each precisely adjusted according to a virtually adjusted consecutive tooth arrangement structure of all of the tooth image. Accordingly, precision of a digital bracket manufactured based thereon is increased, thereby notably increasing reliability of orthodontic treatment and notably increasing functional and aesthetic satisfaction of the subject.

Third, a jig portion assembled with a particular morsal surface shape of each tooth and a grip protrusion portion on which position information of each of the teeth is displayed are manufactured at a top end of a pad portion and are integrated. Accordingly, the digital bracket may be easily and stably gripped to be fixed at an accurate position of each of the teeth that are orthodontic objects. In addition, since the jig portion and the grip protrusion portion are easily separated from the pad portion whose fixation is complete through a segment edge, convenience of orthodontic treatment may be notably increased.

BEST MODE FOR INVENTION

Exemplary embodiments of the present invention will be described in more detail with reference to the attached drawings.

[Mode for Invention]

Hereinafter, an orthodontic digital bracket using a digital library and a method of manufacturing the same according to an exemplary embodiment of the present invention will be described in detail with reference to the attached drawings.

Figure 1:
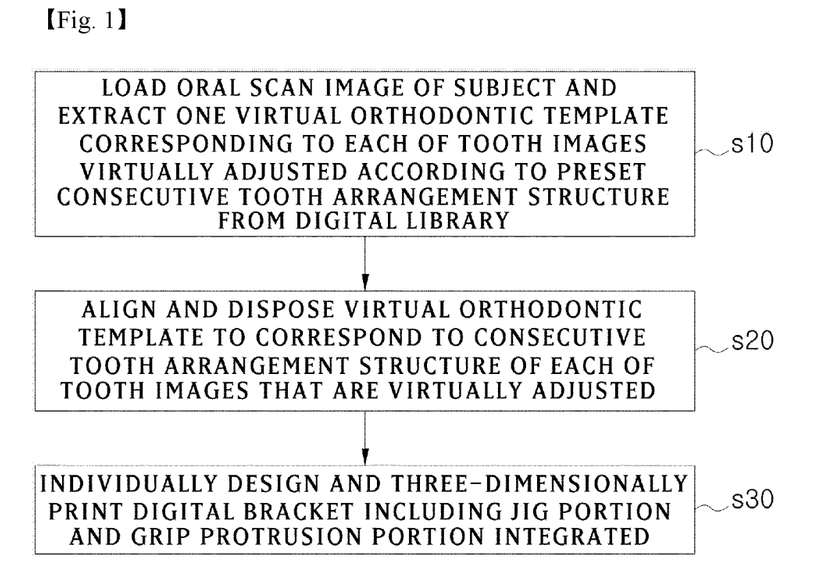
FIG. 1 is a flowchart illustrating a method of manufacturing an orthodontic digital bracket using a digital library according to one embodiment of the present invention.
Figure 2:
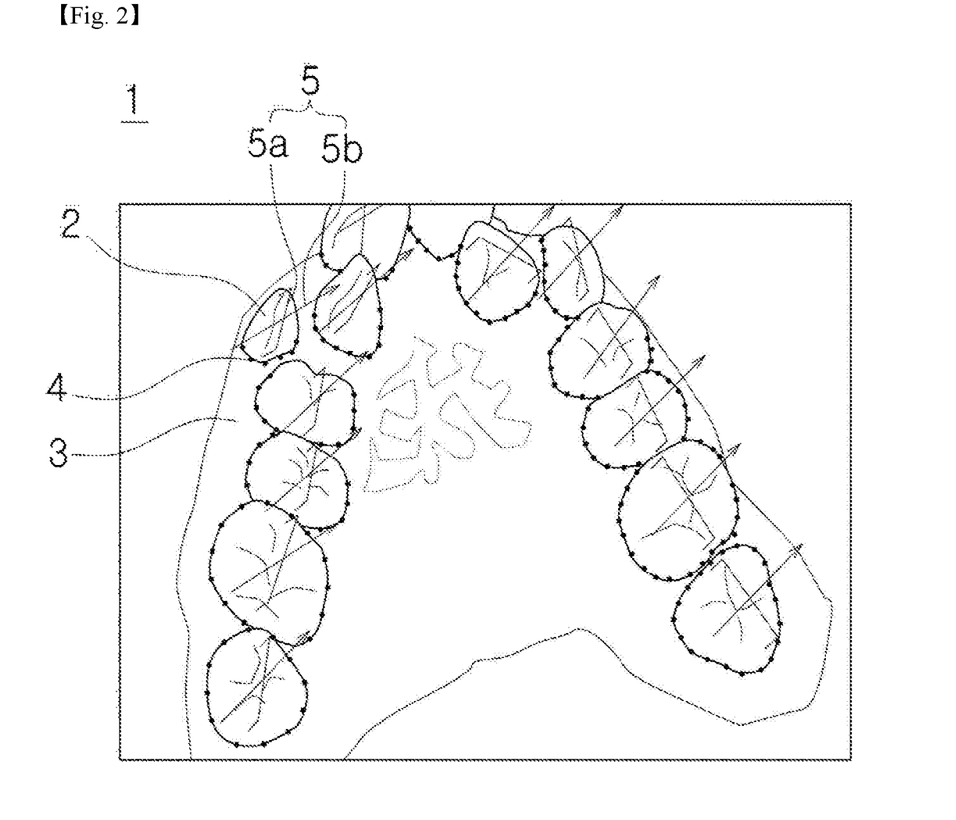
FIG. 2 is a schematic diagram illustrating a process of adjusting an oral scan image in the method of manufacturing an orthodontic digital bracket using a digital library according to one embodiment of the present invention.
Figure 3:
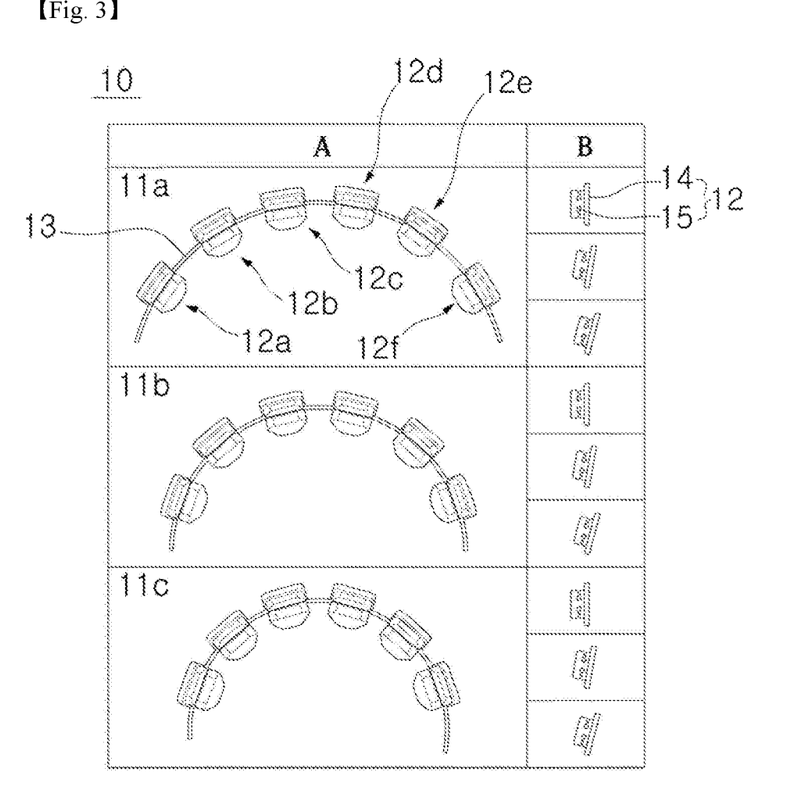
FIG. 3 is a schematic diagram illustrating the digital library in the method of manufacturing an orthodontic digital bracket using a digital library according to one embodiment of the present invention.
Figure 4:
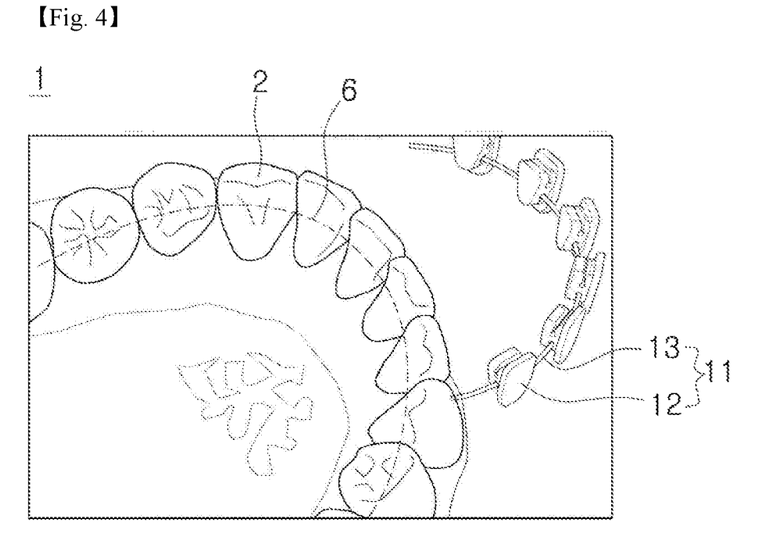
FIG. 4 is a schematic diagram illustrating a process of disposing a virtual orthodontic template in the method of manufacturing an orthodontic digital bracket using a digital library according to one embodiment of the present invention.
Figure 5:
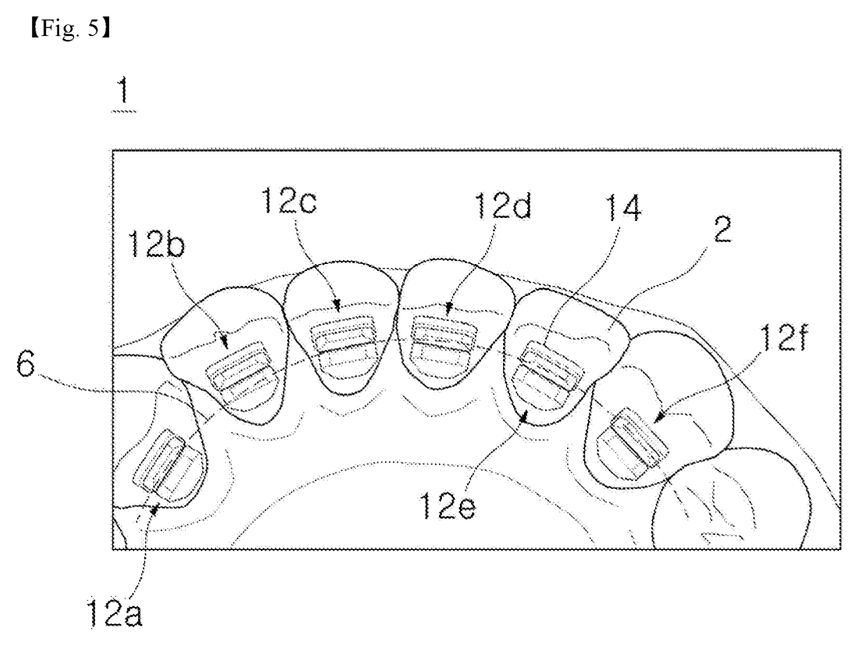
FIG. 5 is a schematic diagram illustrating a process of finely adjusting a position of a virtual bracket corresponding to a tooth arrangement in the method of manufacturing an orthodontic digital bracket using a digital library according to one embodiment of the present invention.
Figure 6:
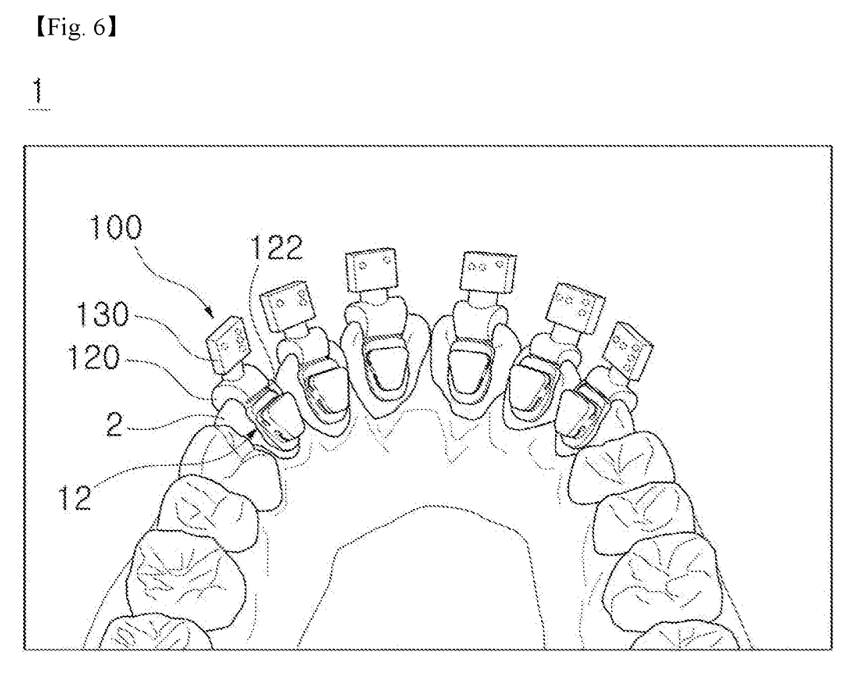
FIG. 6 is a schematic diagram illustrating a process of designing a bracket including a jig portion and a grip protrusion portion in the method of manufacturing an orthodontic digital bracket using a digital library according to one embodiment of the present invention.
Figure 7A:
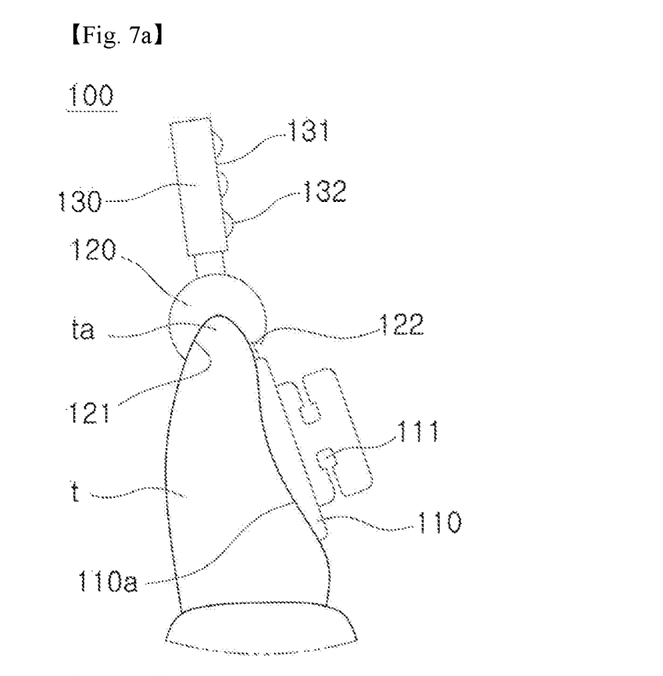
FIGS. 7a and 7b are views illustrating a process of installing a digital bracket manufactured according to the method of manufacturing an orthodontic digital bracket using a digital library according to one embodiment of the present invention.
Figure 7B:
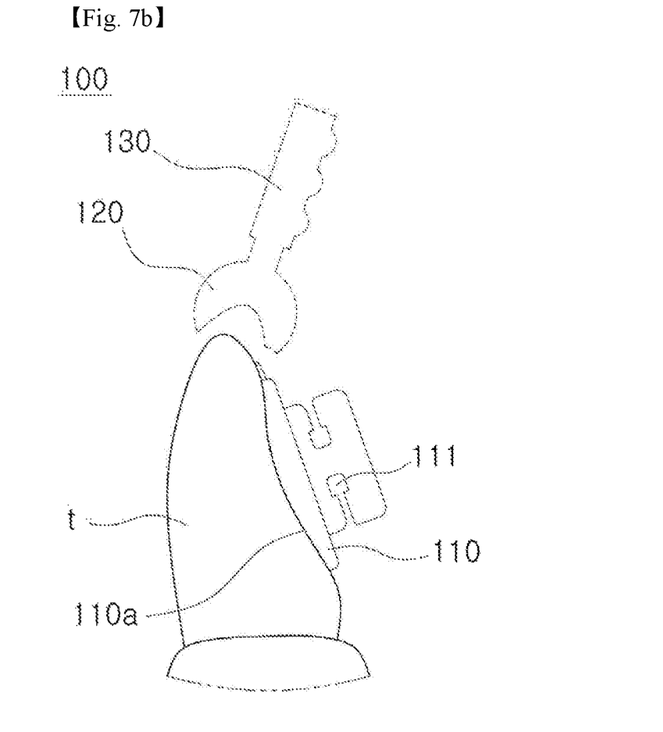

FIG. 1 is a flowchart illustrating a method of manufacturing an orthodontic digital bracket using a digital library according to one embodiment of the present invention. Also, FIG. 2 is a schematic diagram illustrating a process of adjusting an oral scan image in the method of manufacturing an orthodontic digital bracket using a digital library according to one embodiment of the present invention. FIG. 3 is a schematic diagram illustrating the digital library in the method of manufacturing an orthodontic digital bracket using a digital library according to one embodiment of the present invention. Also, FIG. 4 is a schematic diagram illustrating a process of disposing a virtual orthodontic template in the method of manufacturing an orthodontic digital bracket using a digital library according to one embodiment of the present invention. FIG. 5 is a schematic diagram illustrating a process of finely adjusting a position of a virtual bracket corresponding to a tooth arrangement in the method of manufacturing an orthodontic digital bracket using a digital library according to one embodiment of the present invention. Also, FIG. 6 is a schematic diagram illustrating a process of designing a bracket including a jig portion and a grip protrusion portion in the method of manufacturing an orthodontic digital bracket using a digital library according to one embodiment of the present invention. Also, FIGS. 7a and 7b are views illustrating a process of installing a digital bracket manufactured according to the method of manufacturing an orthodontic digital bracket using a digital library according to one embodiment of the present invention.

As shown in FIGS. 1 to 7b, the method of manufacturing an orthodontic digital bracket using a digital library according to the present invention consists of the following processes. Meanwhile, it should be understood that a "digital bracket" which will be described below has a meaning substantially corresponding to a "orthodontic digital bracket." Also, it should be understood that "each tooth" has a meaning substantially corresponding to "each tooth that is an orthodontic object."

First, an oral scan image 1 obtained corresponding to an internal profile of an oral cavity of a subject is loaded. Also, one virtual orthodontic template 11 corresponding to each tooth image 2 virtually adjusted according to a preset consecutive tooth arrangement structure 6 is extracted from a digital library 10 (s10).

Here, it should be understood that the preset consecutive tooth arrangement structure 6 may refer to a virtual dental arch profile corresponding to an orthodontic treatment plan established to straighten a tooth arrangement of the subject to be a preferable functional aesthetic occlusion state.

In detail, the preset consecutive tooth arrangement structure 6 may be established on the oral scan image 1 based on an overall internal structure of the oral cavity of the subject and an experience of an orthodontist.

For example, each of the tooth images 2 included in the oral scan image 1 may be three-dimensionally processed based on an alignment reference portion 5, which will be described below, and then virtually adjusted to correspond to the preset consecutive tooth arrangement structure 6. Also, the digital bracket 100 may be designed on the oral scan image 1 and then manufactured through three-dimensional printing so that teeth of the subject that are orthodontic objects substantially correspond to the preset consecutive tooth arrangement structure 6.

Here, the preset consecutive tooth arrangement structure 6 may be set based on an arched profile of a gum at an upper end portion of an alveolar bone displayed on the oral scan image 1. Also, the preset consecutive tooth arrangement structure 6 may be set based on a tooth arrangement at molars displayed on the oral scan image 1. That is, the preset consecutive tooth arrangement structure 6 may be set according to an estimation of a tooth arrangement state at incisors based on a consecutive tooth arrangement state at the molars with less or no deformation of the tooth arrangement.

In addition, the preset consecutive tooth arrangement structure 6 may be standardized to represent individual deviations such as age, gender, a difference between sizes of upper and lower jaws, and the like and stored in a plurality in a simulation apparatus or a digital library which will be described below.

That is, the orthodontist may select and extract one consecutive tooth arrangement structure corresponding to the inside of the oral cavity of the subject among a plurality of such consecutive tooth arrangement structures prestored in the simulation apparatus or the digital library. Also, each of the tooth images 2 may be virtually adjusted to be the preset consecutive tooth arrangement structure 6 by three-dimensionally processing each of the tooth images 2 in the oral scan image 1 to correspond to the extracted consecutive tooth arrangement structure.

Meanwhile, the oral scan image 1 includes the tooth image 2 and a gum image 3 in the oral cavity in which teeth in the upper jaw and lower jaw of the subject that are orthodontic objects and need orthodontic treatment are included. Here, the oral scan image 1 may be obtained by scanning only one side of the inside of the oral cavity including the teeth that are the orthodontic objects, but may be obtained together with a scan image of the upper and lower jaws in consideration of a functional aesthetic occlusion relationship with a substitutive occlusal tooth.

The oral scan image 1 described above may be obtained by directly scanning the inside of the oral cavity of the subject, and may be obtained by scanning an impression model taken from the inside of the oral cavity of the subject. Here, the obtained oral scan image 1 may be converted into three-dimensional vector data and stored to be easily image-processed through image conversion.

Meanwhile, the oral scan image 1 may be obtained by the orthodontist, stored in a terminal of an orthodontist side, transmitted to a server of a manufacturer through a wired or wireless communication network, and then image-processed by the manufacturer.

Here, the orthodontist side should be understood as a general dental clinic in which orthodontic treatment is actually performed. Also, the terminal of the orthodontist side may refer to a medium in which the oral scan image 1 obtained by the orthodontist is stored and may be provided as a personal computer (PC) or an additional data processor.

Also, the manufacturer should be understood as a treatment support center for manufacturing dental prostheses (brackets, wires, and the like) necessary for orthodontic treatment using three-dimensional vector data of the oral scan image 1 provided from the terminal of the orthodontist side. Also, the server of the manufacturer is an apparatus in which information transmitted from the terminal of the orthodontist side is stored and includes a simulation apparatus capable of performing three-dimensional image processing for designing dental prostheses for orthodontics adequate for a subject.

That is, loading of the oral scan image 1 should be understood as referring to loading the oral scan image 1 onto the simulation apparatus for three-dimensional image processing after the oral scan image 1 stored in the terminal of the orthodontist side is transmitted to the server of the manufacture.

An impression model corresponding to the inside of the oral cavity of the subject may be manufactured by the orthodontist and delivered to the manufacturer, and then the manufacturer may scan the impression model to obtain the oral scan image 1. Additionally, the orthodontist may visit the manufacturer and may obtain the oral scan image 1 using an oral scanner provided at the manufacturer.

Also, the terminal of the orthodontist side and the server of the manufacturer may perform wired or wireless two-way communication with each other. That is, the server of the manufacturer may receive information stored in the terminal of the orthodontist side, and the terminal of the orthodontist side may receive information stored in the server of the manufacturer or mutually share information with the server of the manufacturer.

Meanwhile, the obtained oral scan image 1 may be divided into each of the tooth images 2 and the gum image 3 through image analysis, and may be image-processed to separate each of the tooth images 2 from the gum image 3.

In detail, referring to FIG. 2, a plurality of boundary points 4 are set along a boundary between each of the tooth images 2 and the gum image 3 displayed in the oral scan image 1. Also, an area may be set by connecting lines between the boundary points 4 set adjacently to each other, and each of the tooth images 2 may be separated from the gum image 3. Here, as a space between the boundary points 4 is reduced, each of the tooth images 2 may be more clearly and precisely separated from the gum image 3.

Here, the boundary points 4 may be manually designated and set on the simulation apparatus by the manufacturer, and may be automatically set on the oral scan image 1 based on a preset boundary area designating algorithm.

For example, the algorithm may have a designated value set based on a color difference between each of the tooth images 2 and the gum image 3 in the oral scan image 1. Also, positions and spaces of the boundary points 4 between each of the tooth images 2 and the gum image 3 may be automatically set according to the set designated value. In addition to the color difference described above, they may also be set based on various designated values for distinguishing each of the tooth images 2 from the gum image 3. Additionally, the boundary points 4 automatically set as described above may be manually corrected through reanalyzing an image at the manufacturer and may be more clearly separated from each of the tooth images 2 through the reanalysis.

Here, since an implantation position and angle may be different according to each tooth inside the oral cavity of the subject, the tooth images 2 displayed in the oral scan image 1 may be individually separated. Through this separation, since it is possible to three-dimensionally process each of the tooth images 2 corresponding to the preset consecutive tooth arrangement structure 6, a clearer orthodontic treatment plan may be established.

In addition, the gum image 3 may also be virtually adjusted into a shape surrounding a bottom of each of the tooth images 2 virtually adjusted according to the preset consecutive tooth arrangement structure 6. Accordingly, since an overall orthodontic state of the inside of the oral cavity may be estimated through the oral scan image 1 while each of the tooth images 2 are virtually adjusted, accuracy of orthodontic treatment may be more improved. The gum image 3 separated from each of the tooth images 2 may be deleted from the oral scan image 1, and such a modification of an image processing method belongs within the scope of the present invention.

Also, the alignment reference portion 5 may be set at each of the tooth images 2, and each of the tooth images 2 may be three-dimensionally processed based on the alignment reference portion 5 and virtually adjusted to correspond to the preset consecutive tooth arrangement structure 6.

Here, the alignment reference portion 5 may include a first reference line 5*a* which connects a central portion with both ends of each of the tooth images 2 and guides lateral movement thereof and a second reference line 5*b* which guides longitudinal movement corresponding to an implantation angle of the each tooth. Here, the three-dimensionally processing and movement should be understood as three-dimensional operations capable of rotating and shifting a position and angle for virtually adjusting each of the tooth images 2 corresponding to a preferable tooth arrangement, that is, the preset consecutive tooth arrangement structure 6.

That is, each of the tooth images 2 may be rotated and moved to be virtually adjusted so that both adjacent ends of the first reference line 5*a* to form a continuous arch shape based on the preset consecutive tooth arrangement structure 6. Also, positions and angles of each of the tooth images 2 and the substitutive occlusal tooth may be three-dimensionally processed and virtually adjusted based on the second reference line 5*b* to form a preferable functional aesthetic occlusion state.

Accordingly, according to the present invention, precise design information of the digital bracket may be provided through the oral scan image 1 obtained corresponding to the inside of the oral cavity of the subject and virtually adjusted with the preset consecutive tooth arrangement structure 6. Also, an orthodontic treatment plan may be established considering a functional and aesthetic occlusion relationship between teeth of the subject that are orthodontic objects and substitutive occlusal teeth through the oral scan image 1. Through this, a period of the orthodontic treatment may be notably reduced and satisfaction of the subject with the treatment through the orthodontic treatment may be notably improved.

Here, to establish a more precise and accurate orthodontic treatment plan, a computed tomography (CT) scan image corresponding to the inside of the oral cavity of the subject may be further obtained. That is, since information on an implantation direction and length of a dental root, alveolar bone density, and the like of a tooth may be further obtained through the CT scan image, a more stable and accurate orthodontic treatment plan may be established.

Here, each of the tooth images 2 may be manually adjusted corresponding to the preset consecutive tooth arrangement structure 6 based on each of the reference lines 5*a* and 5*b* of the alignment reference portion 5. Each of the reference lines 5*a* and 5*b* of the alignment reference portion 5 may be automatically aligned and matched with the consecutive tooth arrangement structure 6, and a modification of the image processing method is included within the scope of the present invention.

Meanwhile, one virtual orthodontic template 11 is selected and extracted from the digital library 10 to correspond to each of the tooth images 2 virtually adjusted according to the preset consecutive tooth arrangement structure 6.

Referring to FIGS. 3 and 4, the digital library 10 may include digital external shape information of a plurality of such virtual orthodontic template 11. Here, the virtual orthodontic templates 11 are classified according to selection items, such as a dental arch profile, a tooth type, an arrangement interval, and an angle, standardized to represent individual deviations according to gender and age.

In detail, the digital library 10 includes a plurality of pieces of digital external shape information of virtual orthodontic templates 11*a*, 11*b*, and 11*c* including a plurality of virtual brackets 12*a*, 12*b*, 12*c*, 12*d*, 12*e*, and 12*f* respectively corresponding to teeth and a virtual wire 13 connecting the virtual brackets. Here, the digital external shape information should be understood as referring to three-dimensional vector data capable of reproducing an external shape and structure of a digital bracket.

That is, the digital external shape information of the virtual bracket 12 may be connected to a manufacturing system, and may be converted into design information of a digital bracket. Accordingly, when one virtual orthodontic template 11 is selected, an overall shape of a digital bracket corresponding to each tooth may be quickly and precisely designed and manufactured without additional design or measurement.

Here, the digital external shape information of the virtual bracket 12 may include digital external shape information of a pad portion 14 directly attached to a tooth and a coupling groove portion 15 with which a wire for providing tension is coupled. Accordingly, the digital bracket may be easily designed and manufactured from the digital external shape information of the virtual bracket 12.

Meanwhile, the virtual orthodontic templates 11*a*, 11*b*, and 11*c* may be subdivided and classified based on each of the selection items. In detail, the virtual orthodontic templates 11*a*, 11*b*, and 11*c* may be primarily classified (A) by calculating and designating average values of a dental arch profile and an arrangement interval between teeth for each gender and age as the selection items. Also, the virtual orthodontic templates 11*a*, 11*b*, and 11*c* primarily classified (A) as described above may be secondarily classified (B) by calculating and designating an average value of implantation angles of teeth as the selection item.

Accordingly, one virtual orthodontic template 11 corresponding to the preset consecutive tooth arrangement structure 6, which is preset according to the subject, may be easily obtained and quickly aligned and disposed at each of the tooth images 2 virtually adjusted in the oral scan image 1. Also, since the plurality of virtual brackets 12*a*, 12*b*, 12*c*, 12*d*, 12*e*, and 12*f* may be simultaneously disposed at respective teeth that are orthodontic objects, design and manufacturing times may be notably reduced. Here, since the plurality of virtual brackets 12*a*, 12*b*, 12*c*, 12*d*, 12*e*, and 12*f* are substantially aligned with the same line and disposed by the virtual wire 13, aligning and disposing of a virtual bracket may be quickly performed.

In addition, a reference value corresponding to the selection item may be easily calculated form the oral scan image 1. Also, as soon as the calculated reference value is designated as the selection item and input, one virtual orthodontic template corresponding to the preset consecutive tooth arrangement structure 6 of the subject from the digital library 10 may be selected and extracted.

Here, the extracted virtual orthodontic template 11*a* is stored as a set in which the plurality of virtual brackets 12*a*, 12*b*, 12*c*, 12*d*, 12*e*, and 12*f* are connected by the virtual wire 13 corresponding to the preset consecutive tooth arrangement structure 6. Accordingly, since it is possible to virtually dispose the extracted virtual orthodontic template 11*a* at each of the tooth images 2 virtually adjusted in the oral scan image 1, a process of designing dental prostheses and consumed time for orthodontic treatment may be notably reduced.

Here, the virtual orthodontic template 11 corresponds to each of the tooth images 2 and may be provided to match with six particular anterior teeth at which malocclusion frequently occurs.

That is, the virtual brackets 12*a*, 12*b*, 12*c*, 12*d*, 12*e*, and 12*f* may be set to be limited to the anterior teeth which substantially need orthodontic treatment except molars with less deformation of tooth arrangement. Accordingly, since the number of three-dimensionally processed images is minimized, the digital bracket 100 may be quickly manufactured.

Meanwhile, the virtual bracket 12 and the virtual wire 13 of the virtual orthodontic template 11 are aligned and disposed corresponding to the consecutive tooth arrangement structure 6 of each of the tooth images 2 virtually adjusted (s20).

In detail, referring to FIG. 5, the respective virtual brackets 12*a*, 12*b*, 12*c*, 12*d*, 12*e*, and 12*f* are consecutively virtually arranged at one of an outer surface and an inner surface of each image of a tooth that is an orthodontic object. In more detail, the virtual brackets 12*a*, 12*b*, 12*c*, 12*d*, 12*e*, and 12*f* may be virtually disposed at the inner surface of each of the tooth images 2, respectively. Here, the inner surface of each of the tooth images 2 should be understood as a portion corresponding to the inside of the oral cavity, that is, a portion facing the tongue and palate, and the outer surface should be understood as a portion in contact with inner surfaces of lips.

Accordingly, digital brackets based on the digital external shape information of the virtual brackets 12*a*, 12*b*, 12*c*, 12*d*, 12*e*, and 12*f* may be designed and manufactured to be attached to the inner surface of the teeth. Through this, since the digital bracket is not exposed outside during an orthodontic treatment period, aesthetic satisfaction may be increased and occurrence of damage caused by a protruding external surface portion of the digital bracket scratching the inside of the lips or pain and inconvenience caused thereby may be minimized.

Also, the virtual brackets 12*a*, 12*b*, 12*c*, 12*d*, 12*e*, and 12*f* are stored as digital external shape information in a state of being connected by the virtual wire 13 in the digital library 10. Accordingly, the virtual brackets 12*a*, 12*b*, 12*c*, 12*d*, 12*e*, and 12*f* may be simultaneously virtually arranged in the oral scan image 1 while being arranged at consecutive positions, and may be aligned corresponding to each of the tooth images 2 by finely adjusting each of the virtual brackets. Through this, time for designing and manufacturing a digital bracket is notably reduced and orthodontic precision may be notably increased corresponding to each tooth.

Meanwhile, a morsal surface occluding a substitutive occlusal tooth and for masticating food is formed at the inner surface of each tooth and is differently formed for each tooth. Accordingly, the virtual brackets 12*a*, 12*b*, 12*c*, 12*d*, 12*e*, and 12*f* included in the virtual orthodontic template 11 may be simultaneously disposed to correspond to the tooth images 2, respectively, and may be individually adjusted according to a disposition angle and a morsal surface of each of the teeth.

In addition, the virtual brackets 12*a*, 12*b*, 12*c*, 12*d*, 12*e*, and 12*f* may be adjusted to dispose each of the teeth at a position straightened by tension of a wire appropriate for the preset consecutive tooth arrangement structure 6.

Here, respective positions in which the virtual brackets 12*a*, 12*b*, 12*c*, 12*d*, 12*e*, and 12*f* are disposed may be calculated through a process of virtually adjusting a three-dimensional position of each of the tooth images 2 in the oral scan image 1 to correspond to the preset consecutive tooth arrangement structure 6. That is, since the positions of the virtual brackets 12*a*, 12*b*, 12*c*, 12*d*, 12*e*, and 12*f* in the oral scan image 1 are precisely calculated and used as design information for manufacturing a digital bracket, precision of orthodontic treatment may be further increased.

Meanwhile, when the virtual brackets 12*a*, 12*b*, 12*c*, 12*d*, 12*e*, and 12*f* are respectively aligned with the tooth images 2 corresponding to the preset consecutive tooth arrangement structure 6 (s20), the digital bracket 100 for orthodontics is designed. Also, the digital bracket 100 is three-dimensionally printed based on design data (s30).

Here, a jig portion 120 assembled to surround a top of each of the tooth images 2 and a grip protrusion portion 130 configured to protrude from a top end of the jig portion 120 may be designed above each of the virtual brackets 12 and be integrated.

Here, the digital bracket 100 is manufactured based on the virtual orthodontic template 11 aligned and disposed according to the consecutive tooth arrangement structure 6 of each of the tooth images 2 virtually adjusted in the oral scan image 1. Accordingly, since precision of orthodontic treatment using the digital bracket 100 is notably improved, functional and aesthetic satisfaction of the subject may be notably increased.

In detail, referring to FIGS. 6 to 7*b*, the jig portion 120 is designed to extend from a top end of the virtual bracket 12, that is, a top end of a pad portion 110, and be assembled with an outer surface of a top end of each of the tooth images 2.

Here, the pad portion 110 is set according to digital external shape information of one virtual orthodontic template 11 extracted from the digital library 10 to correspond to the each of the tooth images 2 virtually adjusted according to the preset consecutive tooth arrangement structure 6.

In detail, the pad portion 110 includes at least one coupling groove portion 111 with one side corresponding to each of the teeth of the subject that are orthodontic objects and the other side coupled with a wire configured to provide tension to straighten a position of each of the teeth that are orthodontic objects.

Here, the pad portion 110 may be formed to have a narrower width toward a dental root of each of the teeth than a width toward a top end of a crown of the tooth. That is, since the pad portion 110 is formed to substantially correspond to a profile of each of the teeth getting narrower from the crown to the root, the pad portion 110 may be more stably coupled with each of the teeth.

Also, as shown in the drawings, the coupling groove portion 111 may be formed with multiple stages at a top end and a bottom end or may be formed with one stage traversing a central portion. Also, the coupling groove portion 111 may be formed to laterally pass through the other side of the pad portion 110 or an upwardly or downwardly open opened groove may be further formed.

In addition, the coupling groove portion 111 may pass through the pad portion 110 as a slot hole shape extending in a longitudinal direction thereof. Here, the wire may be provided in a flat shape with different thicknesses and widths of a cross section corresponding to an internal profile of the coupling groove portion 111.

In addition, the coupling groove portion 111 may be directly formed at the pad portion 110 to pass therethrough or may be formed at a protrusion portion integrated with the other side of the pad portion 110 to intensively provide tension of the wire. Here, the protrusion portion may be formed to be smaller than an area of the pad portion 110.

Meanwhile, the jig portion 120 is designed at the top end of the virtual bracket 12, which is virtually disposed at a position for straightening a position of each of the teeth using the tension of the wire, to be adequate for the preset consecutive tooth arrangement structure. Here, the top end of the virtual bracket 12 should be understood as substantially being the top end of the pad portion 110.

In detail, the jig portion 120 may be provided at and integrated with the top end of the pad portion 110 while surrounding an outer surface of a top end ta of each of teeth t that is an orthodontic object to be assembled therewith. That is, when an inner surface of the jig portion 120 is assembled with the outer surface of the top end ta of each of the teeth t and fixed thereto, the pad portion 110 may be aligned and fixed at a preset position of each of the teeth t. Here, the preset position of each of the teeth should be understood as a position at which the tension of the wire is applied to straighten each of the teeth t corresponding to the preset consecutive tooth arrangement structure 6.

Here, as the jig portion 120 is designed based on an external profile of the top end of each of the tooth images 2, the digital bracket 100 that is manufactured through three-dimensional printing may be guided to be precisely disposed to be assembled with one side of each of the teeth. That is, when the jig portion 120 is assembled with the outer surface of the top end to of each of the teeth t and fixed thereto, the pad portion 110 may be aligned and fixed to a preset position of each of the teeth t. Here, the preset position of each of the teeth should be understood as a position at which tension of the wire is applied to straighten each of the teeth t corresponding to the preset consecutive tooth arrangement structure 6.

In addition, an assembling groove portion 121 that is assembled with a distinguishing morsal surface of each of the teeth may be formed at the inner surface of the jig portion 120. Accordingly, the digital bracket 100 may be more precisely aligned and disposed at the preset position of each of the teeth using a simple method of fixing the assembling groove portion 121 to be assembled with a particular morsal surface profile of each of the teeth t. Since each of the teeth that are orthodontic objects is precisely straightened according to an orthodontic treatment plan through this, reliability of orthodontics may be notably increased.

Here, since the particular morsal surface shape of each of the teeth is calculated from the oral scan image 1, convenience of designing the jig portion 120 may be further improved.

Here, the digital bracket 100 at a fixed position aligned by the jig portion 120 may be fixed to each of the teeth by applying an adhesive to the inner surface of the pad portion 110.

Meanwhile, a segment edge 122 partially incised to be segmented by an external force may be formed a boundary portion between the pad portion 110 and the jig portion 120.

In detail, the segment edge 122 may be designed to have a thinner thickness than a thickness of a peripheral portion so that the digital bracket 100 may be separated from the pad portion 110 and fixed to each of the teeth. For example, the segment edge 122 may be designed in a slit shape that splits along the boundary portion or may be formed in a wedge groove shape such as 'v' shape and 'u' shape. In addition, the segment edge 122 may be formed in a broken line with alternating through holes and connected portions, and is not limited as long as a shape is configured to enable the jig portion 120 to be separable form the pad portion 110 of the digital bracket 100.

Accordingly, the digital bracket 100 according to the present invention may be easily aligned and fixed at the preset position of each of the teeth at which tension of the wire 3 is precisely applied through the jig portion 120. Also, when a certain force is applied, the jig portion 120 whose use is complete may be easily separated using the segment edge 122. Since the digital bracket 100 may be quickly fixed to a precise position through this, accuracy and convenience of treatment may be notably improved and inconvenience in daily life may be reduced.

In addition, the jig portion 120 and the segment edge 122 are simultaneously designed based on the oral scan image 1 obtained and virtually adjusted to design the digital bracket 100. Also, instantaneous manufacturing using the design information is possible and precision is also notably improved.

Here, the pad portion 110 may be disposed to correspond to one side of each of the teeth t and an assembling mounting portion 110*a* assembled with the particular morsal surface profile of each of the teeth t may be further set at the inner surface of the pad portion 110.

Accordingly, the digital bracket 100 may be guided to a more accurate position by precisely assembling an internal surface profile connected to the assembling mounting portion 110*a* with an external profile of each of the teeth t at the assembling groove portion 121. Accordingly, reliability of orthodontic treatment may be notably improved.

Meanwhile, the grip protrusion portion 130 that protrudes and extends may be provided at the top end of the pad portion 110 for easy gripping. Here, the top end of the pad portion 110 should be understood as substantially being an upward direction of the jig portion 120.

In detail, the grip protrusion portion 130 may protrude upward and have a preset gripping area to enable the orthodontist to easily grip the grip protrusion portion 130. Accordingly, the orthodontist may easily move to the inside of the oral cavity of the subject and fix the digital bracket 100 while directly gripping the grip protrusion portion 130 with a hand. An additional gripping means such as tweezers and the like may be used to grip the grip protrusion portion 130.

Here, the grip protrusion portion 130 extends by a certain length while having the preset gripped area. Accordingly, since the pad portion 110 and the coupling groove portion 111 may be prevented from coming into contact with each other, hygiene of the digital bracket 100 may be notably improved even when the orthodontist directly grips the grip protrusion portion 130 with the hand.

In addition, as the grip protrusion portion 130 protrudes to a preset height, a position at which an external force is applied and the segment edge 122 may be spaced apart by a certain distance. Accordingly, the segment edge 122 may be easily broken even though a small force is applied to the grip protrusion portion 130 according to the principle of levers. Since the jig portion 120 and the grip protrusion portion 130 are simultaneously separated through this, convenience of treatment may be further improved and inconvenience for the subject may be minimized while the digital bracket 100 is fixed.

Meanwhile, a marking portion 131 on which notification information on a type and a position of each of the teeth are displayed may be formed at an end of the grip protrusion portion 130.

In detail, the marking portion 131 includes notification information on each of the teeth corresponding to each of the digital brackets 100. That is, on the marking portion 131, notification information on whether a tooth is a left tooth or a right tooth based on a midline (ML) in the oral cavity, what number anterior tooth or canine tooth it is, and the like may be displayed. Also, when tooth arrangements of upper and lower jaws are simultaneously straightened, the marking portion 131 may further include notification information on whether the digital bracket 100 corresponds to the upper jaw or lower jaw. For example, when one of the digital brackets 100 corresponds to a canine tooth of a left side of the lower jaw, notification information corresponding thereto may be displayed on the marking portion 131.

In addition, the notification information may be symbolized and protrude as raised letters 132. For example, the information on the canine tooth at the left side of the lower jaw may be symbolized as the raised letters 132 and may protrude from an outer surface of the marking portion 131.

Accordingly, since the orthodontist may clearly recognize the information on the tooth only through information transferred by touch while gripping the grip protrusion portion 130 with the hand, accuracy and convenience may be notably improved. Also, since slippage is prevented while the orthodontist grips the grip protrusion portion 130, it is possible to provide a more stable grip.

The information may be symbolized and displayed as letters, numbers, and a combination thereof, and modifications described above belong within the scope of the present invention.

Meanwhile, when the jig portion 120, the grip protrusion portion 130, and the segment edge 122 are designed to be integrated at the top end of the virtual bracket 12 in the digital external shape information of the virtual bracket 12 and the oral scan image 1, the jig portion 120, the grip protrusion portion 130, and the segment edge 122 are manufactured through three-dimensional printing.

Here, since the digital bracket 100 is designed based on the digital external shape information of the virtual bracket 12 prestored in the digital library 10, inconvenience caused by individually designing the bracket may be removed.

Also, the jig portion 120 is designed to be assembled with a top end profile of each of the tooth images 2 while the marking portion 131 with position information of each of the tooth images 2 is formed at the top end of the grip protrusion portion 130. Accordingly, the digital bracket 100 that is three-dimensionally printed may be easily aligned and fixed to a preferable position of each of the teeth.

Meanwhile, a length of a wire connecting each of the digital brackets 100 may be calculated from the virtual wire 13 of the virtual orthodontic template 11 adjusted to correspond to the consecutive tooth arrangement structure 6 of each of the tooth images 2 that are virtually adjusted. That is, since the orthodontist may prepare the wire based on length information of the virtual wire 13 calculated in the oral scan image 1, convenience of orthodontic operation may be further improved.

Figure 8:
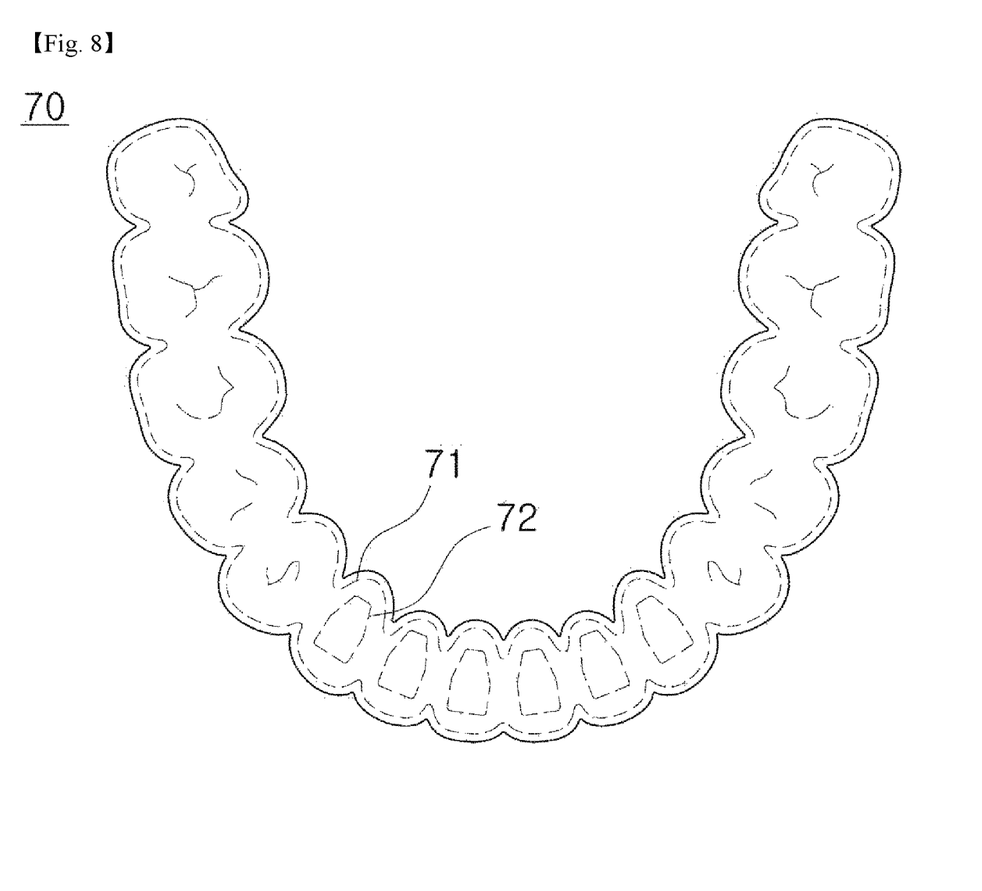
FIG. 8 is a schematic diagram illustrating a retainer apparatus in the method of manufacturing an orthodontic digital bracket using a digital library according to one embodiment of the present invention.

Meanwhile, FIG. 8 is a schematic diagram illustrating a retainer apparatus in the method of manufacturing an orthodontic digital bracket using a digital library according to one embodiment of the present invention.

As shown in FIG. 8, a retainer apparatus 70 may be further designed and manufactured when a digital bracket is designed so that the digital bracket may remain in a state of being installed and fixed to each of the teeth.

The retainer apparatus 70 described above is installed to surround the inside of the oral cavity of the subject, the digital bracket, and the wire configured to provide tension for orthodontics by connecting the same. Accordingly, orthodontic efficiency and precision in orthodontic treatment using the digital bracket may be further improved.

Here, the retainer apparatus 70 may be manufactured including a first cover groove portion 71 configured to cover the inside of the oral cavity at the teeth of the subject that are orthodontic objects and a second cover groove portion 72 configured to cover the digital bracket and the outside of the wire. Here, the first cover groove portion 71 and the second cover groove portion 72 may be provided to surround an outside of the teeth that are orthodontic objects, the digital bracket, and an outside of the wire and be substantially closely fixed thereto.

Accordingly, the teeth that are orthodontic objects may be covered with a combination of the digital brackets and the wire and the retainer apparatus 7, thereby being precisely and accurately straightened.

Also, when the first cover groove portion 71 and the second cover groove portion 72 are installed in the oral cavity of the subject while being coated with a whitening agent, a fluoride compound, or the like, a portion difficult to be finely washed may be tidily managed by the digital brackets and wire. Through this, hygiene inside the oral cavity of the subject may be further improved during an orthodontic treatment period.

Here, the retainer apparatus 70 may be designed in an oral scan image. That is, in the oral scan image, virtual brackets are virtually arranged, a virtual wire is connected to mutually connect the virtual brackets, and the cover groove portions 71 and 72 corresponding to an external profile thereof are designed. Also, the retainer apparatus may be easily designed by designing an external portion thereof to protrude from each of the cover groove portions 71 and 72 by a preset thickness.

Here, a thickness of the retainer apparatus 70 may be designed to fix the digital bracket and the wire and minimize inconvenience in masticating while installed in the oral cavity of the subject.

Also, the retainer apparatus 70 may be formed of a transparent or translucent synthetic resin material having a certain elastic force. Accordingly, the retainer apparatus 70 is elastically deformed corresponding to external profiles of the teeth that are orthodontic objects, the digital brackets, and the wire in order to be easily installed. Also, since it is possible to provide a pressure and fixing force according to an elastically restoring force to the teeth that are orthodontic objects when the retainer apparatus 70 is in an installation state, orthodontics may be more precisely and stably performed.

In addition, the retainer apparatus 70 may be formed of a transparent or translucent synthetic resin material.

That is, since not only the digital bracket 100 for orthodontic treatment but also the retainer apparatus configured to assist the orthodontic treatment may be easily designed in the oral scan image 1 and manufactured through three-dimensional printing, quickness of orthodontic treatment and convenience of use may be notably improved.

Accordingly, according to the present invention, since digital external shape information of one of the virtual orthodontic templates 11 may be simply and quickly connected to design information of the digital bracket 100 reversely, convenience of manufacturing a digital bracket may be notably increased. Here, the one of the virtual orthodontic templates 11 may be selected corresponding to the preset consecutive tooth arrangement structure 6 of the subject among the plurality of virtual orthodontic templates 11 prestored in the digital library 10 to represent personal deviations.

Here, in case of the virtual orthodontic template 11, the plurality of virtual brackets 12 are stored as one set. Also, the virtual brackets 12 are simultaneously arranged in the oral scan image 1 corresponding to the inside of the oral cavity of the subject and are individually finely adjusted according to the virtually adjusted consecutive tooth arrangement structure 6 of each of the tooth images 2. Accordingly, the precision of the digital bracket 100 manufactured based thereon is increased, thereby notably increasing reliability of orthodontic treatment and notably increasing functional and aesthetic satisfaction of the subject.

In addition, the jig portion 120 assembled with the particular morsal surface shape of each of the teeth and the grip protrusion portion 130 on which position information of each of the teeth is displayed are manufactured at the top end of the pad portion 110 and integrated. Accordingly, the digital bracket 100 may be easily and stably gripped to be fixed at an accurate position of each of the teeth that are orthodontic objects. Also, since the jig portion 120 and the grip protrusion portion 130 are easily separated from the pad portion 110 whose fixing is complete by the segment edge 122, convenience may be notably increased.

In addition, a result of orthodontic treatment considering a functional and aesthetic occlusion state of the subject may be virtually calculated by three-dimensionally processing each of the tooth images 2 in the oral scan image 1. Accordingly, the digital bracket 100 for more precise and accurate orthodontics may be manufactured based thereon.

While the embodiments of the present invention have been described, the present invention is not limited to each of the embodiments described above and may be modified by one of ordinary skill in the art without departing from the scope of the present invention defined by the claims of the present invention, and equivalents thereof belong to the scope of the present invention.

INDUSTRIAL APPLICABILITY

The present invention is applicable to the field of manufacturing orthodontic apparatuses by providing an orthodontic digital bracket using a digital library and a method of manufacturing the same.

The invention claimed is:

1. An orthodontic bracket, comprising:
a pad portion including a first side corresponding to a surface of a tooth of a subject, and a second side opposite to the first side and having a coupling groove portion configured to be coupled with a wire configured to provide tension to straighten a position of each of teeth;
a jig portion integrally formed with the pad portion as a single body and extended from a top of the pad portion to surround an external surface of a top end of the tooth to align a position of the pad portion, wherein the jig portion includes:
an assembling portion extended downward from a vertex of the jig portion and configured to surround the external surface of the top end of the tooth; and
an assembling groove portion formed on an inner surface of the assembling portion and configured to be assembled corresponding to a morsal surface shape;
a segment edge being partially incised along a boundary portion between the pad portion and the jig portion and configured to be broken by an external force using a principle of levers to split the pad portion and the jig portion along the segment edge; and
a grip protrusion portion integrally formed with and protruding upward from the vertex at a top center of the jig portion to be gripped, and having a preset height and a grip area so as to break the segment edge by the principle of levers when the external force is applied to the grip protrusion portion,
wherein the grip area includes a marking portion on which notification information on a type and a position of each of the teeth is formed, the notification information being symbolized and protruding from the grip area as raising letters.

* * * * *